United States Patent [19]

Jacobs

[11] Patent Number: 4,950,253

[45] Date of Patent: Aug. 21, 1990

[54] NEEDLE EJECTOR STRUCTURE FOR A SYRINGE

[76] Inventor: Jerome Jacobs, 6415 Allison Rd., Miami Beach, Fla. 33141

[21] Appl. No.: 319,090

[22] Filed: Mar. 6, 1989

[51] Int. Cl.⁵ ............................................ A61M 5/315
[52] U.S. Cl. .................................... 604/218; 604/240; 604/243
[58] Field of Search ............... 604/181, 187, 218, 228, 604/232, 235, 240, 243

[56] References Cited

U.S. PATENT DOCUMENTS

| 3,259,130 | 7/1966 | Krauthamer | 604/228 |
| 3,537,453 | 11/1970 | Drummond | 604/232 |
| 3,838,690 | 10/1974 | Friedman | 604/228 |
| 4,333,458 | 6/1982 | Margulies et al. | 604/228 |

Primary Examiner—Stephen C. Pellegrino
Assistant Examiner—Michael Rafa
Attorney, Agent, or Firm—Malloy & Malloy

[57] ABSTRACT

A needle ejector structure to be used with a syringe and structurally adapted to be removably inserted therein and driven into driving, disengaging relation to a connected hub portion of a needle upon forced travel of the plunger associated with the syringe thereby enabling separation and ejection of the needle from the syringe after use without the necessity of the needle or hub portion thereof being touched by medical personnel. Danger of contamination by inadvertent puncture when removing the needle is thereby eliminated.

11 Claims, 2 Drawing Sheets

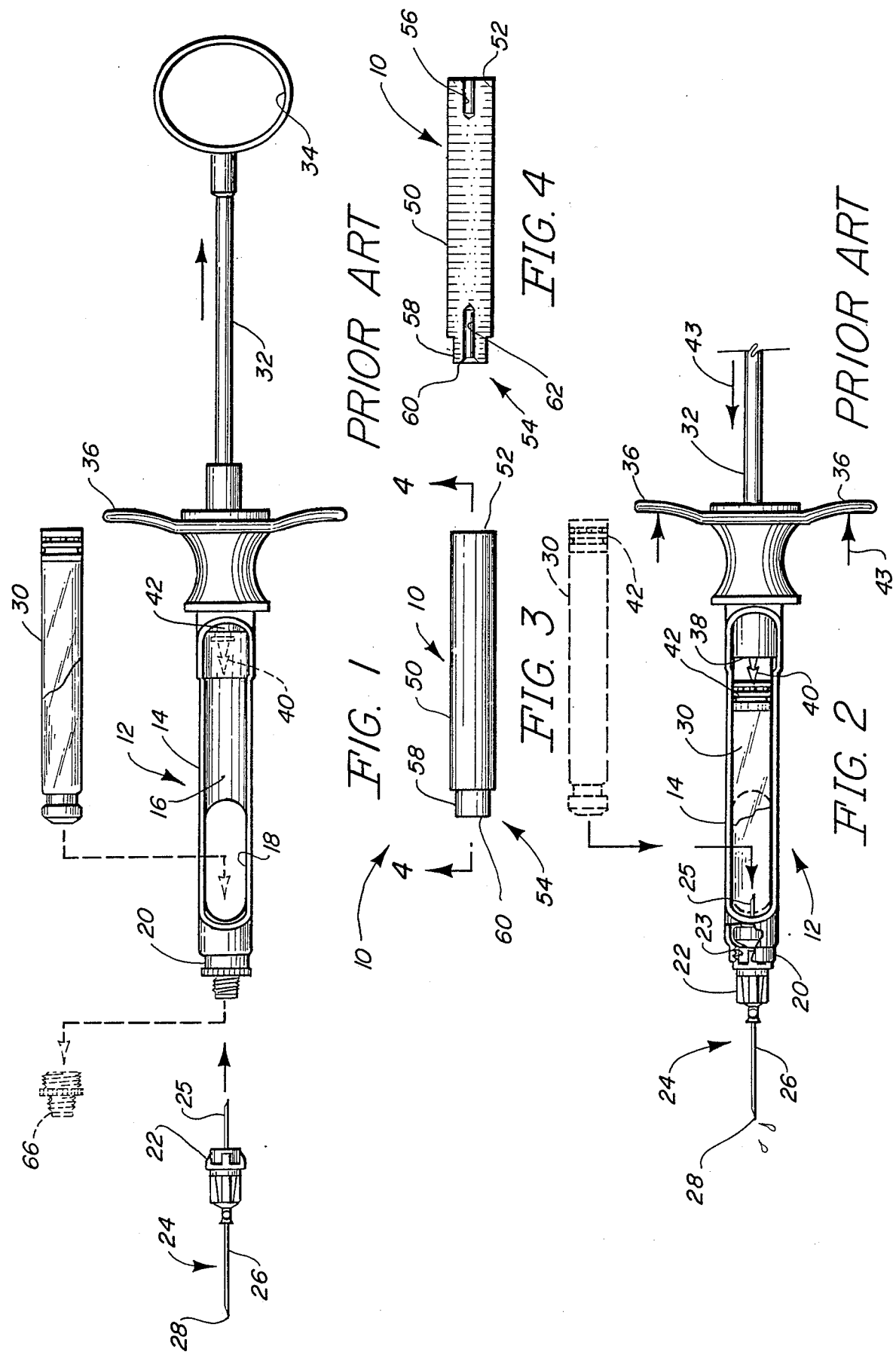

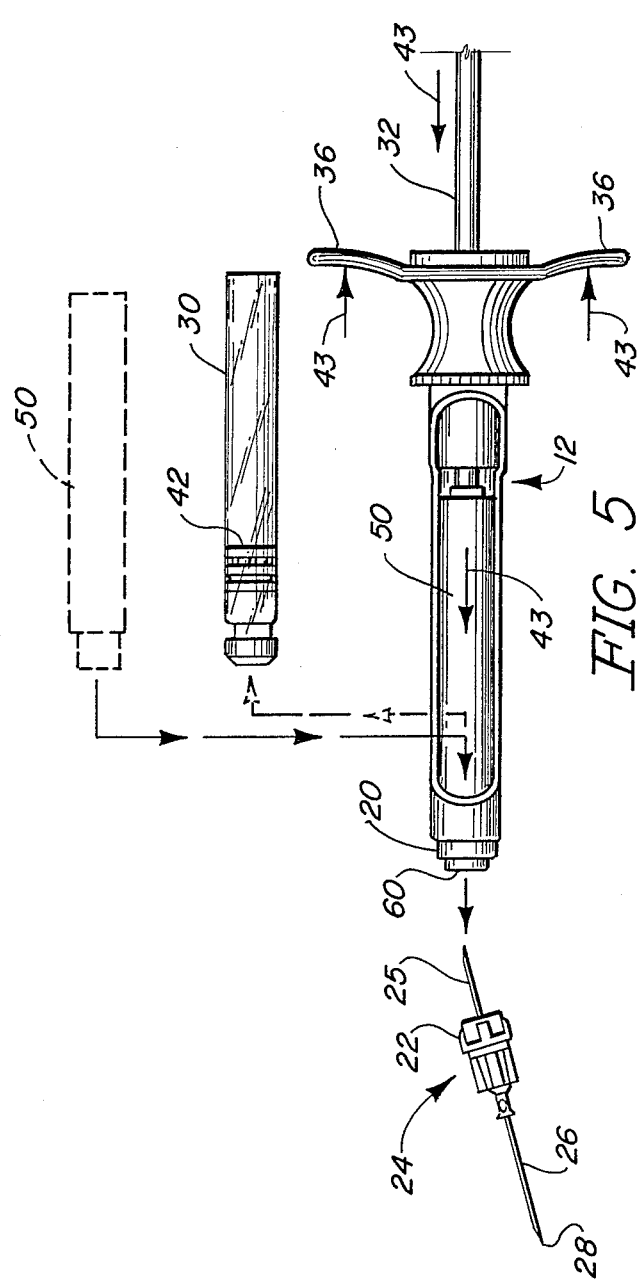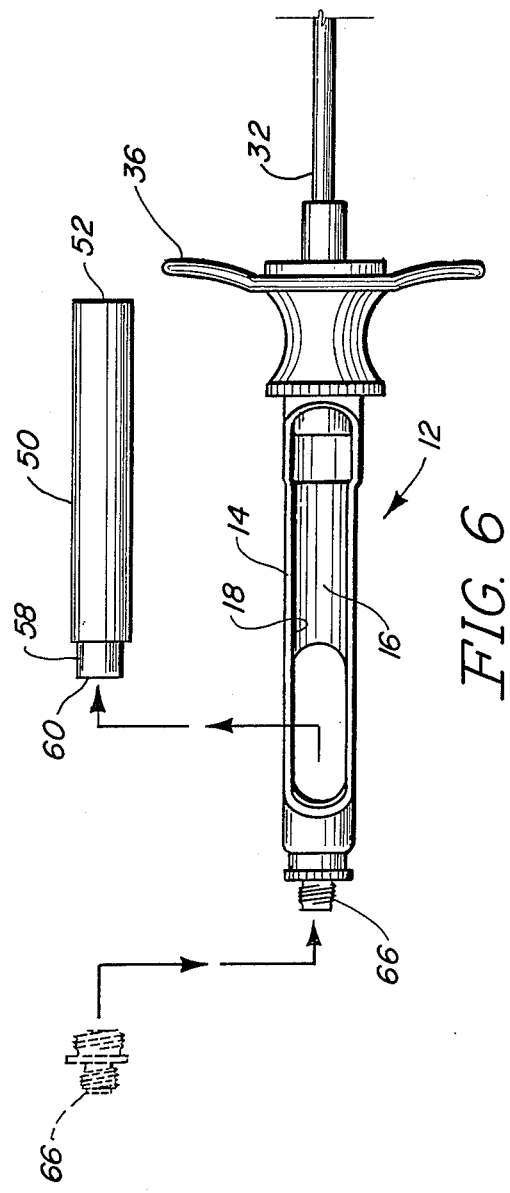
FIG. 5
FIG. 6

NEEDLE EJECTOR STRUCTURE FOR A SYRINGE

BACKGROUND OF THE INVENTION

1. Field of the Invention

An ejector structure is removably inserted within a reusable type syringe and is adapted to accomplish separation of a needle structure from the distal end of the syringe after use without necessitating the handling of the needle or distal end of the syringe to which the needle is mounted.

2. Description of the Prior Art

The use of needles in both the dental and medical profession for the injection (or removal) of bodily fluid into the human body is of course extremely widespread and a common practice in patient care. In dentistry, it is normal practice to inject a local anesthetic so that the required procedures can be accomplished without undue pain or discomfort to the patient. Due to the advances in modern technology, numerous structural modifications have been made with the hypodermic syringe and the like. Numerous structures are presently in use which are now intended and designed to be disposable after a single use in order that infectious and contagious deceases cannot be spread from one patient to another such as when a needle is reused. However, particularly in the field of dentistry, a reusable syringe is commonly used to apply the above-noted anesthetic. Such a conventional syringe structure includes an elongated barrel having a slot extending along at least a portion of one wall thereof and communicating with the interior for the insertion of a cartridge containing the fluid intended to be injected. This type of syringe also includes a plunger having a barbed or spiked distal end which moves telescopically along the interior of the barrel and engages a stopper structure associated with the cartridge for purposes of driving or forcing the contents of the cartridge out through an attached hub portion of a needle. The hub portion is removably secured to an open distal end of the barrel by a threaded engagement therewith. Forcing of the proximal end of the plunger, using pressure exerted thereon both by the thumb and fingers, forces the plunger telescopically along the interior of the barrel. This movement of the plunger also forces the stopper within the cartridge to travel along its interior until the desired amount of fluid passes therefrom into the patient through the attached needle.

After use, it is common practice for medical personnel to detach, as by unscrewing or the like, the hub portion of the needle from the distal end of the barrel for purposes of disposal. However, such handling of the needle structure for purposes of detachment from the barrel has resulted in inadvertent contact with the sharpened point of the needle. This obviously subjects the medical personnel handling the needle and syringe to the spreading of contagious or infectious deceases. Such risks have become particularly important in recent years due to the spread of potentially fatal deceases, such as but not limit to ACQUIRED IMMUNE DEFICIENCY SYNDROME (AIDS). The latter decease is of course of particular concern since there is no known cure. Further, it has been scientifically established that one method of transferring this decease is through the use of contaminated needles.

Accordingly, there is a need in the medical and dental profession as well as the associated instrument industry for a structure or assembly capable of being used with a nondisposable syringe structure of conventional design which allows for the separation and/or ejection of the needle from the distal end of the barrel of the syringe subsequent to use thereof without requiring handling of the needle or touching of the syringe in the area of the distal end thereof. Such separation of the previously connected hub portion of the needle and therefore ejection of the needle itself may further be accomplished without recapping the used needle or mounting any type of protective cover over the sharpened end thereof.

A preferred solution to the above set forth problems should be particularly adapted for use in combination with a reusable or permanent type syringe particularly of the type to apply local anesthetic, such as Novocain or the like, to inner portions of the mouth, through injection. Such means of safely separating or ejecting the hub portion of the needle from the syringe is of course required since the typical syringe of the type used in dental procedures of the type set forth above are not intended to be disposable.

SUMMARY OF THE INVENTION

The present invention is directed towards a structure of the type to be used with a conventional reusable syringe such as a Cooke-Waite dental syringe for the separation and/or ejection of a used, contaminated needle from the distal end thereof without personnel coming into direct contact with the needle or its connecting hub portion or the distal end of the barrel of the syringe to which the needle is attached. It should be emphasized that the subject invention is adaptable for use with syringes other than the specific type mentioned above.

The needle ejector structure of the present invention comprises a push rod having a elongated configuration and preferably being formed of a rigid material in an integral, one piece construction. The push rod is specifically dimensioned to pass through an elongated slot formed in the barrel of the syringe. Such an elongated slot is utilized for the insertion and removal of an anesthetic or like material containing cartridge. The conventional syringe structure of the type set forth herein includes a movable plunger having a distal end with a barbed configuration for removable attachment to a stopper portion on the interior of the cartridge. Forced travel of the plunger telescopically along the interior of the barrel, when engaged with the stopper of the cartridge, serves to force fluid within the cartridge out through the attached hub and needle assembly removably secured to the open, distal end of the barrel. A proximal end of the needle protrudes outwardly through a corresponding end of the hub portion and penetrates the opposite end of the cartridge for fluid communication therewith.

Typically, after use, the cartridge is removed from the interior of the barrel and the hub portion of the now contaminated needle is detached from the distal end of the barrel by unthreading or otherwise breaking the interconnection thereto. This procedure is of course effective in removal and disposal of the needle and attached hub portion. However, an obvious danger associated with this procedure relates to the increased tendency for the medical personnel handling the assembly to become inadvertently stuck, and thereby potentially contaminated, by the sharpened point of the used needle.

Accordingly, the present invention comprises an ejector structure in the form of the elongated push rod dimensioned and configured to fit within the elongated slot of the barrel and be positioned on the interior thereof. A proximal end of the push rod is specifically configured to receive the barbed, proximal end of the plunger in a manner which will allow confronting engagement with this end of the plunger without damage being done to the barb extending outwardly from this end. Such structural adaptation is preferably in the form of an opening, elongated channel, or the like dimensioned to receive substantially the full length of the barb on the interior of the push rod.

Similarly, the opposite or distal end of the push rod is specifically adapted to pass at least partially through the open distal end of the barrel into confronting, engaging relation with the removably secured hub portion of the needle. Similarly, this distal end of the push rod is structurally adapted, through the provision of preferably a coaxial channel formed on the interior thereof, to receive the proximal end of the needle protruding outwardly from the hub into the interior of the barrel.

It should be apparent therefor that upon forced movement of the plunger and specifically the barbed end telescopically within the barrel towards the open distal end thereof, confronting, driving engagement of the barbed end with a corresponding proximal end of the push rod will occur. Continued movement at least a minimal distance of the plunger will cause the equivalent axial movement of the push rod and a confronting, driving engagement between the distal end of the push rod and the hub portion of the needle assembly. This forced movement will cause a breaking or separation of the interconnection of the hub to the distal end of the barrel and an ejection and separation of the needle and hub portion thereof from the barrel entirely. Such ejection can occur directly into a disposal facility thereby eliminating the necessity for any medical personnel coming into direct contact with the needle, the removable hub portion or the distal end of the barrel to which it is attached. After ejection of the needle, the push rod can be easily removed from the interior of the barrel in the same manner that a used cartridge is removed therefrom.

The invention accordingly comprises the features of construction, combination of elements and arrangement of parts which will be exemplified in the construction hereinafter set forth and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is a front plan view partially exploded of a conventional, prior art syringe.

FIG. 2 is a front plan view of a prior art syringe including a cartridge and attached needle structure in partial cutaway.

FIG. 3 is a front plan view of a push rod structure of the present invention.

FIG. 4 is a cross-sectional view along line 4—4 of FIG. 3 of the push rod embodiment.

FIG. 5 is a front plan view in partial cutaway with the push rod of the embodiments of FIGS. 3 and 4 inserted in the subject syringe.

FIG. 6 is a front plan view in partial cutaway showing removal of the push rod and attachment of an adaptor-type nose piece to the syringe structure.

Like reference numerals refer to like parts throughout the several views of the drawings.

DETAILED DESCRIPTION OF THE PREFERRED EMBODIMENT

As shown in FIG. 1 through 6, the present invention is directed towards a needle ejector assembly including an elongated push rod generally indicated as 10 and shown in detail in FIGS. 3 and 4. As will be explained in greater detail hereinafter, the push rod 10 is designed for use in combination with a conventional, prior art syringe 12 such as a Cooke-Waite dental syringe. With reference to FIG. 2, the conventional syringe structure 12 includes an elongated barrel 14 having a hollow interior as at 16 and an elongated slot 18 formed in the wall of the barrel. The slot is disposed to establish access to the interior 16 of the barrel 14. The distal end of the barrel is open as at 20 to receive the hub portion 22 of a needle assembly generally indicated as 24. The needle 26 of course has a sharpened tip for penetration into the patient as at 28 and further includes a proximal end 25 protruding into the interior of the barrel when mounted in the position of FIG. 2 for placement on the interior of a cartridge 30 containing a local anesthetic or like fluid to be injected.

A removable interconnection is established between the open distal end 20 of the barrel 14 and the hub portion 22 by means of internal threads 23 formed on the inner surface of the distal end 20 which mate with a corresponding periphery structurally adapted to establish the removable connection between the hub 22 and the distal end 20.

The syringe 12 also includes an elongated plunger as at 32 having a thumb grip 34 at a distal end thereof. Finger grips 36 are also provided o the barrel 14 in order to allow forced movement of the plunger 32 along the length of the barrel 14 and on the interior thereof. The proximal end of the plunger 32 as at 38 has an outwardly extending barb 40. This barb is designed to engage, through penetration, a stopper member 42 located on the interior of the cartridge 30. Driving forward movement of the plunger in accordance with directional arrow 43 causes the barb to force the plunger 32 along the interior length of the cartridge 30 and thereby drive the fluid out through the needle assembly 24 in conventional fashion.

One obvious problem associated with the operation and workings of the syringe and included cartridge is the removal of the needle assembly 24 after use. The needle assembly 24, being contaminated, presents dangers if such needle is inadvertently penetrates one handling the syringe. Accordingly, the present invention is directed towards the needle ejector assembly 10 including an elongated push rod 50 formed of a rigid material such as metal or plastic and including a proximal end 52 and a distal end generally indicated as 54. The length of the push rod 50 is such as to pass through the elongated slot 18 formed in the barrel 14. In addition, the length of the push rod is such as to clearly fit on the interior 16 of the barrel 14 in a position similar to the cartridge 30 as pictured in FIG. 5.

When in such operative position as shown in FIG. 5, the push rod 50 has its proximal end disposed in confronting relation and engagement with the proximal end 38 of the plunger 32. In such position, the proximal end 38 may serve to drive or force the push rod 50 at least a minimal distance along the length of the barrel 14 and on the interior thereof as shown in FIG. 5. In order to prevent damage to the barb 40 at the barb end of the push rod, the proximal end 52 is specifically structured to have an opening or elongated channel 56 dimensioned and configured both longitudinally and transversely to receive the entire length of the barb 38 therein.

Similarly, the opposite or distal end 54 of the push rod 50 includes a reduced diameter end portion 58 dimensioned to pass into the open distal end 20 of the barrel 14. The extremity thereof as at 60 therefore drivingly engages the correspondingly positioned extremity or end of the hub 22 of the needle assembly 24. Forced movement of the push rod 50 in the direction toward the needle assembly 24 by forced movement of the plunger 32 in accordance with the directional arrow 43 forces a separation of the hub 22 in the open distal end 20 of the barrel. The needle assembly 24, after separation, may therefore be ejected and dispensed into any type of dispensing facility for disposal thereof. Such separation and ejection of the needle assembly 24 from the barrel 14 is accomplished without medical personnel being required to touch the needle assembly 24 or even come in contact with the portion or the barrel 14 adjacent the distal open end 20.

When in such operative position, it is important to note that the distal end 54 of the push rod 50 includes an elongated axially disposed channel or the like 62 disposed and dimensioned to receive the proximal end of the needle normally projecting into the interior 16 of the barrel 14 through the open distal end. Such proximal end of the needle is normally fitted into the interior of the cartridge 30 to receive the fluid therein. This proximal end of the needle is disposed to pass into the interior of the elongated channel 62 after the cartridge 30 is removed from the interior 16 of the barrel 14 and when the push rod 50 is placed on the interior of the barrel in the operative position shown in FIG. 5.

Another feature of the present invention includes the syringe 12 having the nose piece 66 being removed from the open distal end 20 prior to the mounting of the needle assembly 24 therein (see FIG. 2). The nose piece 66 is externally threaded to mate with the internal threads 23 on the interior of the open distal end 20.

FIG. 6 shows removal of the push rod 50 and a reattachment of the nose portion 66 after the needle assembly 24 has been totally detached.

Now that the invention has been described,
What is claimed is:

1. A needle ejector structure for use in a syringe having a plunger having a barbed distal end telescopically positionable within a hollow interior of an elongated barrel and an elongated slot extending along an outer wall of the barrel, the slot dimensioned and disposed to allow passage therethrough of a cartridge into and out of the hollow interior, said barrel including an open distal end structured to removably secure a hub portion of a needle thereto;
said needle ejector structure comprising:
 a. a push rod having an elongated configuration and adapted to pass through the slot into and out of the hollow interior,
 b. said push rod including a proximal end disposed in abutting engagement with the barbed end of the plunger when said push rod is within the hollow interior of the barrel, said push rod being axially movable within said barrel upon engagement with, and telescopic movement of said plunger, and
 c. said push rod further including a distal end structured to pass at least partially through said open distal end of said barrel into abutting engagement with the hub of the needle, therby forcing the hub portion to separate from the distal end of the barrel upon movement of said push rod towards the open distal end.

2. A structure as in claim 1 wherein said proximal end of said push rod is structured to receive a barbed end of the plunger in driving abutting engagement therewith.

3. A structure as in claim 2 wherein said proximal end of said push rod comprises an opening integrally formed therein and dimensioned and disposed to receive a barb secured to said barbed end therein.

4. A structure as in claim 3 wherein said opening comprises an elongated channel formed coaxially within said push rod and having a sufficient length to receive a full length of the barb therein.

5. A structure as in claim 1 wherein said distal end of said push rod includes an elongated channel formed coaxially therein and being of sufficient length to receive a correspondingly positioned end of the needle therein.

6. A structure as in claim 5 wherein said distal of said push rod includes a reduced diameter extremity transversely dimensioned to pass through said distal open end of said barrel and in driving engagement with the hub portion of the needle.

7. A structure as in claim 6 wherein said proximal end of said push rod comprises an opening integrally formed therein and dimensioned and disposed to receive a barb of the barbed end therein.

8. A structure as in claim 7 wherein said opening comprises an elongated channel formed coaxially within said push rod and being of sufficient length to receive a full length of the barb therein.

9. A structure as in claim 1 wherein said push rod is formed of a rigid material.

10. A structure as in claim 9 wherein said push rod is formed of a rigid, integrally formed plastic material of one piece construction.

11. A structure as in claim 12 wherein said push rod is formed of a rigid, metallic material.

* * * * *